US012690882B2

(12) United States Patent
Hunter et al.

(10) Patent No.: US 12,690,882 B2
(45) Date of Patent: Jul. 28, 2026

(54) ULTRASONIC SURGICAL INSTRUMENT WITH AXISYMMETRIC CLAMPING

(71) Applicant: Cilag GmbH International, Zug (CH)

(72) Inventors: Morgan R. Hunter, Cincinnati, OH (US); Brian D. Black, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/748,606

(22) Filed: Jun. 20, 2024

(65) Prior Publication Data

US 2024/0335212 A1 Oct. 10, 2024

Related U.S. Application Data

(63) Continuation of application No. 17/943,826, filed on Sep. 13, 2022, now Pat. No. 12,048,452, which is a continuation of application No. 16/556,625, filed on Aug. 30, 2019, now Pat. No. 11,471,181.

(51) Int. Cl.
| | |
|---|---|
| *A61B 17/32* | (2006.01) |
| *A61B 17/29* | (2006.01) |
| *A61B 17/295* | (2006.01) |

(52) U.S. Cl.
CPC .... *A61B 17/320092* (2013.01); *A61B 17/295* (2013.01); *A61B 2017/2903* (2013.01); *A61B 2017/2947* (2013.01); *A61B 2017/320094* (2017.08)

(58) Field of Classification Search
CPC .......... A61B 17/320092; A61B 17/295; A61B 2017/320094; A61B 2017/2903; A61B 2017/2947
See application file for complete search history.

(56) References Cited

U.S. PATENT DOCUMENTS

| | | | |
|---|---|---|---|
| 5,322,055 | A | 6/1994 | Davison et al. |
| 5,873,873 | A | 2/1999 | Smith et al. |
| 5,980,510 | A | 11/1999 | Tsonton et al. |
| 6,325,811 | B1 | 12/2001 | Messerly |
| 6,500,176 | B1 | 12/2002 | Truckai et al. |

(Continued)

OTHER PUBLICATIONS

International Search Report and Written Opinion dated Oct. 26, 2020, for International Application No. PCT/IB2020/057738, 11 pages.

(Continued)

*Primary Examiner* — Ashley L Fishback
(74) *Attorney, Agent, or Firm* — FBT Gibbons LLP

(57) ABSTRACT

A surgical instrument includes an end effector, and a shaft assembly. The end effector includes an ultrasonic blade, a rotating body, and a clamp arm movable between an open and a closed position. The shaft assembly extends along an axis and includes clamp arm clocking assembly and a clamp arm pivot assembly. The clamp arm clocking assembly can drive the rotating body and the clamp arm between a first clocked position and a second clocked position. The clamp arm pivot assembly includes an actuator body defining a track, where the actuator body can actuate to drive the clamp arm between the open position and the closed position while the actuator body is in a rotational position relative to the ultrasonic blade. The track houses a portion of the clamp arm in the first clocked position and the second clocked position while the actuator body is in the rotational position.

19 Claims, 17 Drawing Sheets

(56) References Cited

U.S. PATENT DOCUMENTS

| | | | |
|---|---|---|---|
| 6,773,444 | B2 | 8/2004 | Messerly |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 8,461,744 | B2 | 6/2013 | Wiener et al. |
| 8,479,969 | B2 | 7/2013 | Shelton, IV |
| 8,573,461 | B2 | 11/2013 | Shelton, IV et al. |
| 8,573,465 | B2 | 11/2013 | Shelton, IV |
| 8,591,536 | B2 | 11/2013 | Robertson |
| 8,602,288 | B2 | 12/2013 | Shelton, IV et al. |
| 8,616,431 | B2 | 12/2013 | Timm et al. |
| 8,623,027 | B2 | 1/2014 | Price et al. |
| 8,663,220 | B2 | 3/2014 | Wiener et al. |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 8,911,460 | B2 | 12/2014 | Neurohr et al. |
| 9,023,071 | B2 | 5/2015 | Miller et al. |
| 9,095,367 | B2 | 8/2015 | Olson et al. |
| 9,301,759 | B2 | 4/2016 | Spivey et al. |
| 9,381,058 | B2 | 7/2016 | Houser et al. |
| 9,393,037 | B2 | 7/2016 | Olson et al. |
| 9,402,682 | B2 | 8/2016 | Worrell et al. |
| 9,949,785 | B2 | 4/2018 | Price et al. |
| 10,034,683 | B2 | 7/2018 | Monroe et al. |
| 10,172,636 | B2 | 1/2019 | Stulen et al. |
| 10,226,274 | B2 | 3/2019 | Worrell et al. |
| 10,342,567 | B2 | 7/2019 | Hibner et al. |
| 11,457,945 | B2 | 10/2022 | Hunter et al. |
| 11,471,181 | B2 | 10/2022 | Hunter et al. |
| 11,612,409 | B2 | 3/2023 | Black et al. |
| 11,690,642 | B2 | 7/2023 | Black et al. |
| 11,712,261 | B2 | 8/2023 | Hunter et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2011/0087212 | A1 | 4/2011 | Aldridge et al. |
| 2012/0116265 | A1 | 5/2012 | Houser et al. |
| 2014/0114293 | A1 | 4/2014 | Jeong et al. |
| 2015/0080924 | A1 | 3/2015 | Stulen et al. |
| 2015/0320438 | A1 | 11/2015 | Weisenburgh, II et al. |
| 2016/0302818 | A1 | 10/2016 | Weisenburgh, II et al. |
| 2016/0302819 | A1 | 10/2016 | Stulen et al. |
| 2017/0202607 | A1 | 7/2017 | Shelton, IV et al. |
| 2017/0245875 | A1 | 8/2017 | Timm et al. |
| 2017/0281217 | A1 | 10/2017 | Hibner |
| 2017/0281218 | A1 | 10/2017 | Timm |
| 2017/0281219 | A1 | 10/2017 | Hibner et al. |
| 2017/0281220 | A1 | 10/2017 | Hibner et al. |
| 2017/0281221 | A1 | 10/2017 | Boudreaux |
| 2019/0021752 | A1 | 1/2019 | Boudreaux |
| 2023/0071969 | A1 | 3/2023 | Hunter et al. |

OTHER PUBLICATIONS

U.S. Appl. No. 61/410,603, entitled "Energy-Based Surgical Instruments," filed Nov. 5, 2010.

ULTRASONIC SURGICAL INSTRUMENT WITH AXISYMMETRIC CLAMPING

CROSS-REFERENCE TO RELATED APPLICATION

This application is a continuation of U.S. patent application Ser. No. 17/943,826, entitled "Ultrasonic Surgical Instrument with Axisymmetric Clamping," filed Sep. 13, 2022, published as U.S. Pat. Pub. No. 2023/0071969, issued as U.S. Pat. No. 12,048,452 on Jul. 30, 2024, which is a continuation of U.S. patent application Ser. No. 16/556,625, entitled "Ultrasonic Surgical Instrument with Axisymmetric Clamping," filed Aug. 30, 2019, and issued as U.S. Pat. No. 11,471,181 on Oct. 18, 2022.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of ultrasonic surgical instruments include the HARMONIC ACER Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; U.S. Pat. No. 9,095,367, issued Aug. 4, 2015, entitled "Flexible Harmonic Waveguides/Blades for Surgical Instruments," the disclosure of which is incorporated by reference herein; U.S. Pat. No. 10,226,274, issued Mar. 12, 2019, entitled "Ultrasonic Surgical Instrument with Articulation Joint Having Plurality of Locking Positions," the disclosure of which is incorporated by reference herein; U.S. Pat. No. 10,034,683, entitled "Ultrasonic Surgical Instrument with Rigidizing Articulation Drive Members," issued Jul. 31, 2018, the disclosure of which is incorporated by reference herein; U.S. Pat. Pub. No. 2016/0302818, published Oct. 10, 2016, now abandoned, entitled "Ultrasonic Surgical Instrument with Movable Rigidizing Member," the disclosure of which is incorporated by reference herein; U.S. Pat. Pub. No. 2016/0302819, published Oct. 20, 2016, now abandoned, entitled "Ultrasonic Surgical Instrument with Articulating End Effector having a Curved Blade," the disclosure of which is incorporated by reference herein; U.S. Pat. No. 10,342,567, issued Jul. 9, 2019, entitled "Ultrasonic Surgical Instrument with Opposing Thread Drive for End Effector Articulation," the disclosure of which is incorporated by reference herein; U.S. Pat. Pub. No. 2015/0320438, published Nov. 12, 2015, issued as U.S. Pat. No. 10,667,835 on Jun. 2, 2020, entitled "Ultrasonic Surgical Instrument with End Effector Having Restricted Articulation," the disclosure of which is incorporated by reference herein; U.S. Pat. Pub. No. 2017/0281217, published Oct. 5, 2017, issued as U.S. Pat. No. 10,492,819 on Dec. 3, 2019, entitled "Surgical Instrument with Dual Mode Articulation Drive," the disclosure of which is incorporated by reference herein; U.S. Pat. Pub. No. 2017/0281218, published Oct. 5, 2017, entitled "Surgical Instrument with Motorized Articulation Drive in Shaft Rotation Knob," issued as U.S. Pat. No. 10,507,034 on Dec. 17, 2019, the disclosure of which is incorporated by reference herein; U.S. Pat. Pub. No. 2017/0281219, published Oct. 5, 2017, entitled "Surgical Instrument with Locking Articulation Drive Wheel," issued as U.S. Pat. No. 10,743,850 on Aug. 18, 2020, the disclosure of which is incorporated by reference herein; U.S. Pat. Pub. No. 2017/0281220, published Oct. 5, 2017, issued as U.S. Pat. No. 10,575,836 on Mar. 3, 2020, entitled "Surgical Instrument with Selectively Locked Articulation Assembly," the disclosure of which is incorporated by reference herein; and U.S. Pat. Pub. No. 2017/0281221, published Oct. 5, 2017, issued as U.S. Pat. No. 10,405,876 on Sep. 10, 2019, entitled "Articulation Joint for Surgical Instrument," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use,"

issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
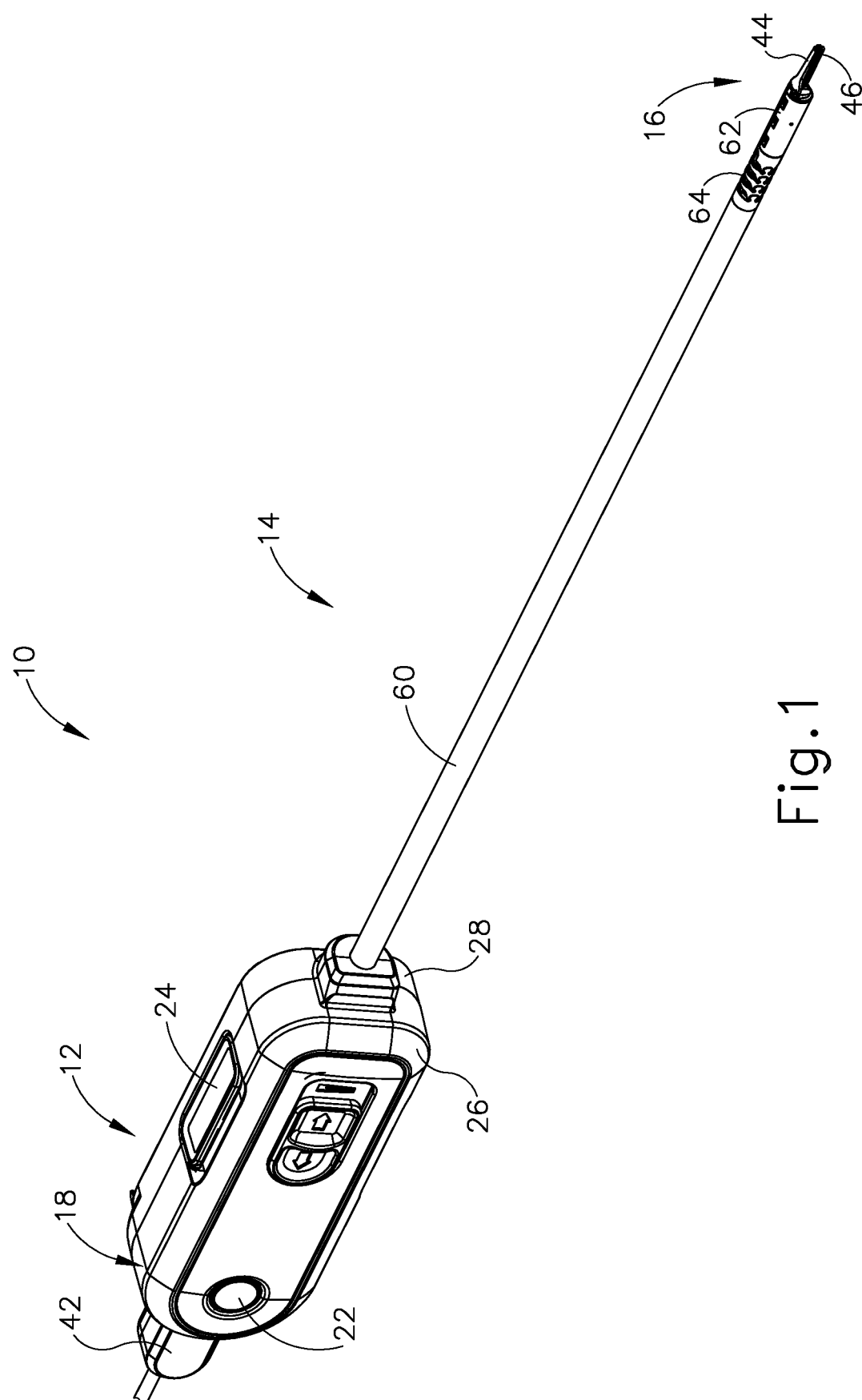
FIG. 1 depicts a front perspective view of an ultrasonic surgical instrument having an end effector, a shaft assembly, and a base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
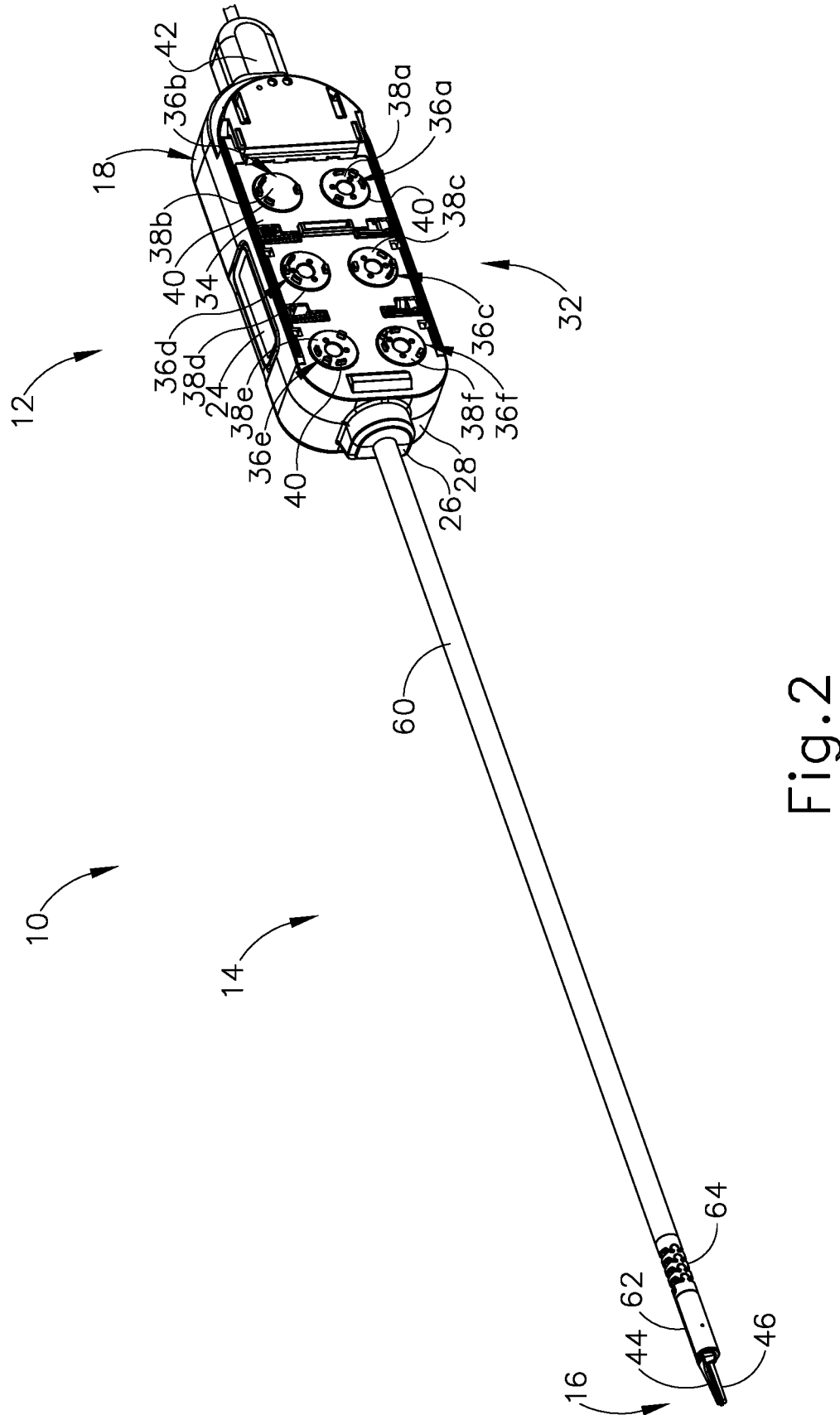
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36c, 36f) having a plurality of input bodies (38a, 38b, 38c, 38d, 38c, 38f), respectively. Each input body (38a, 38b, 38c, 38d, 38c, 38f), which may also be referred to herein as a "puck," is configured to removably connect with the robotic drive (not shown) and, in the present example, is generally cylindrical and rotatable about an axis. Input bodies (38a, 38b, 38c, 38d, 38c, 38f) have a plurality of slots (40) configured to receive portions of the robotic drive (not shown) for gripping and rotatably driving input bodies (38a, 38b, 38c, 38d, 38c, 38f) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
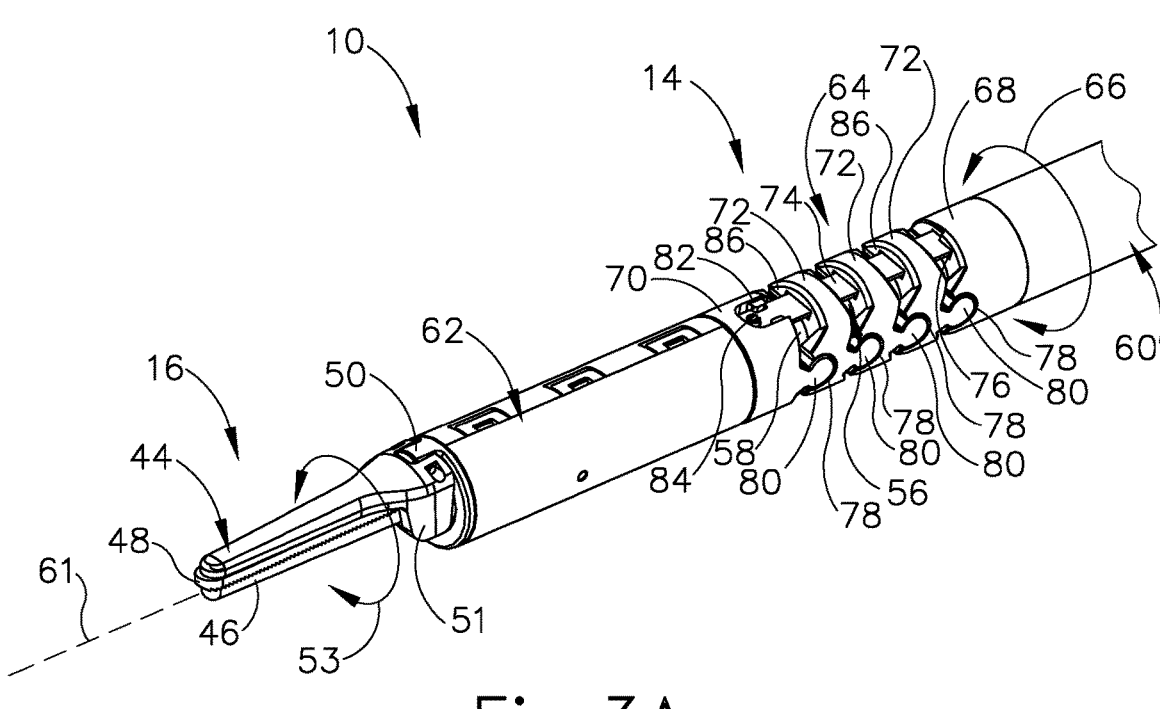
FIG. 3A depicts an enlarged perspective view of the ultrasonic surgical instrument of FIG. 1 with the end effector in a closed position and the shaft assembly in a straight configuration.
Figure 3B:
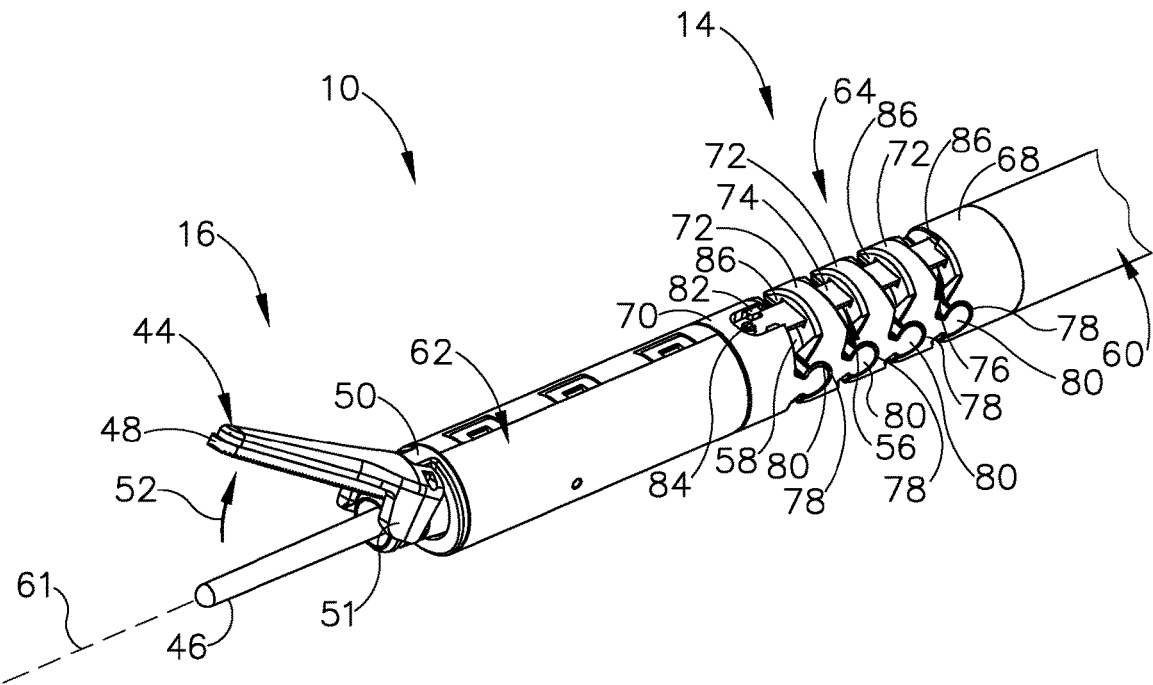
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095, 367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034, 683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
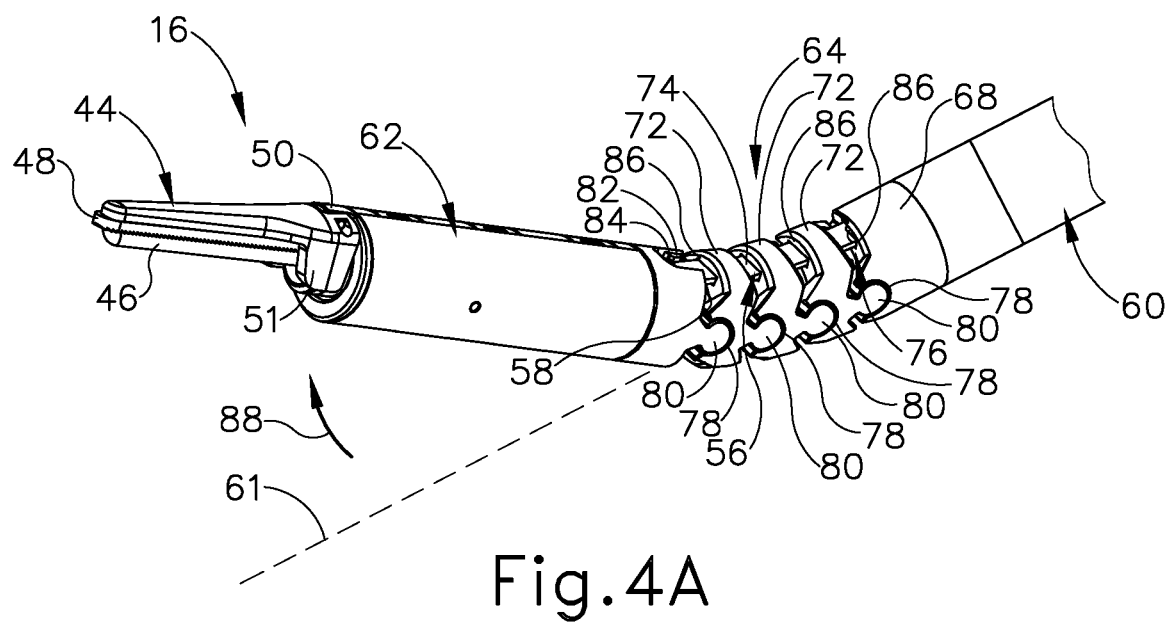
FIG. 4A depicts an enlarged perspective view of the ultrasonic surgical instrument of FIG. 1 with the end effector in a closed position and the shaft assembly in a first articulated configuration.
Figure 4B:
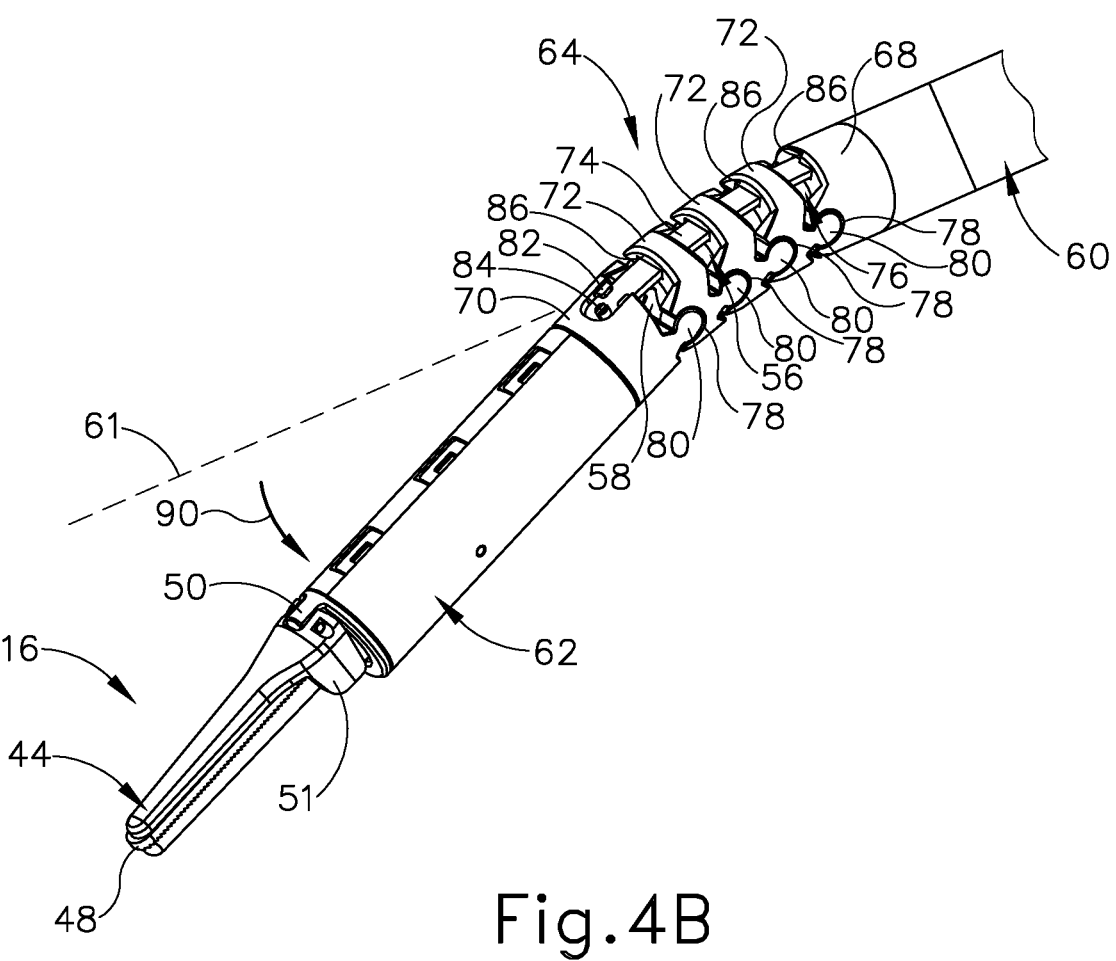
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
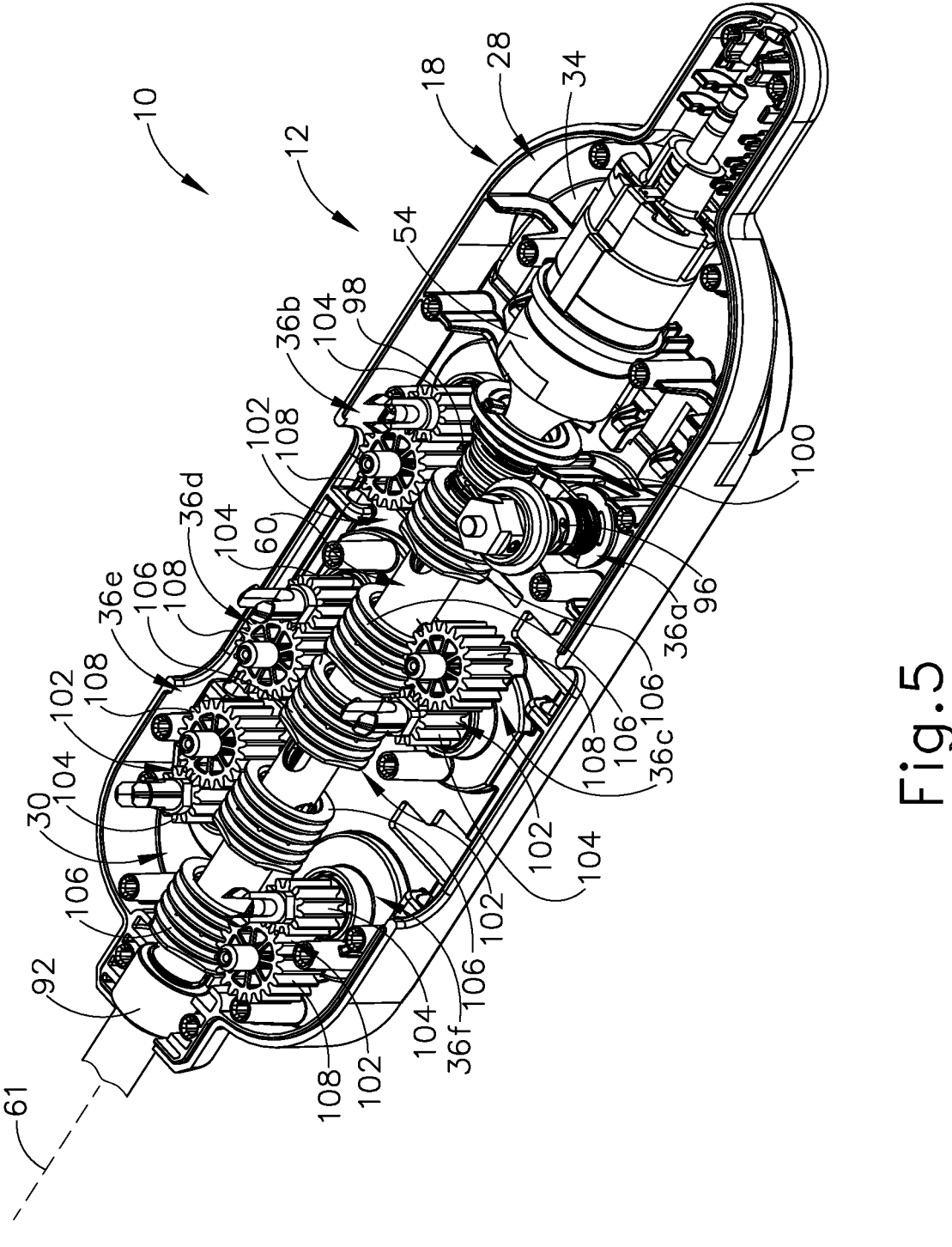
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 36f) in greater detail. Generally, instrument actuators (36a, 36b, 36c, 36d, 36e, 36f) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 36f) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
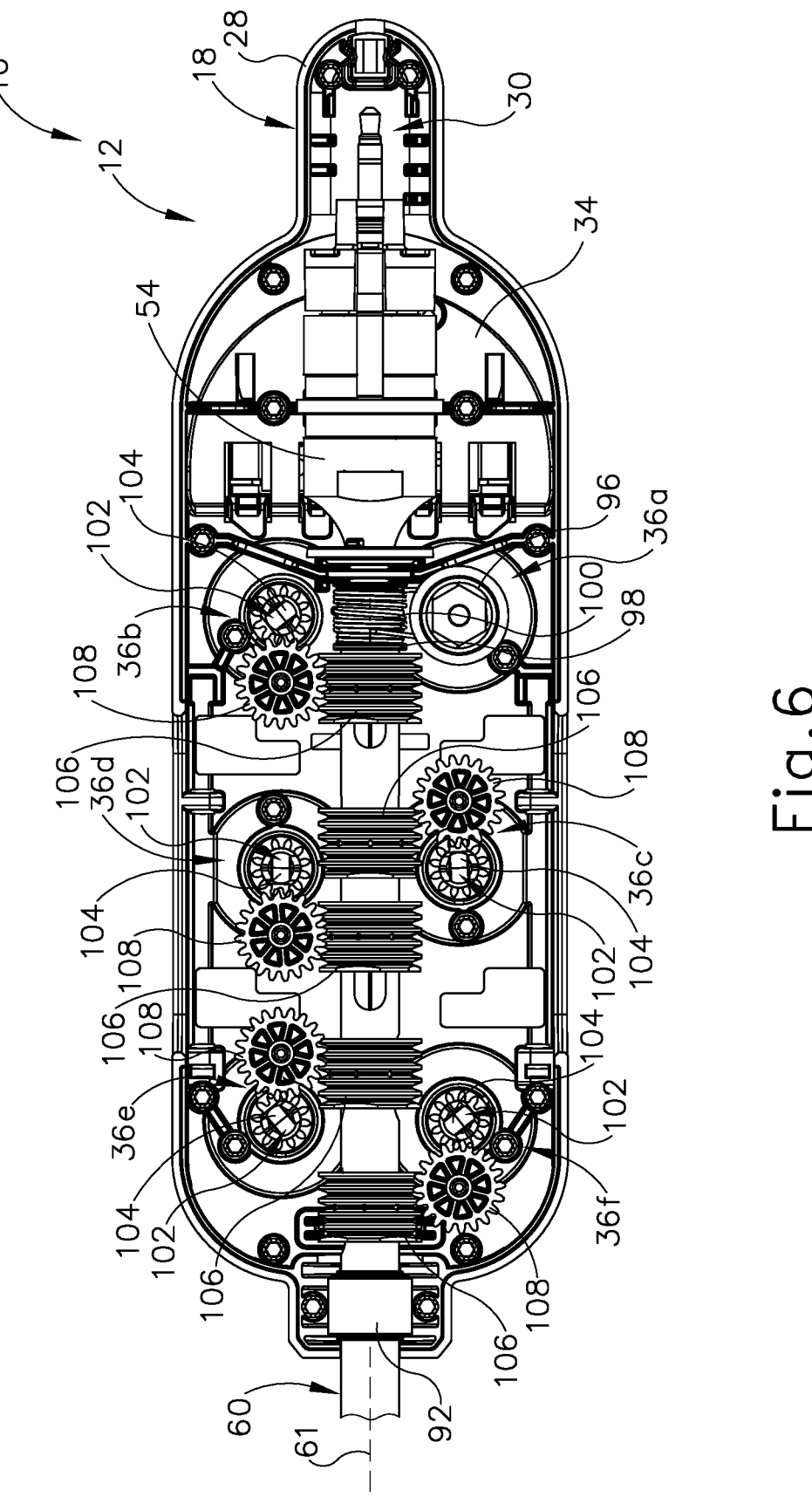
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 36f), although it will be appreciated that any such number of such instrument actuators (36a, 36b, 36c, 36d, 36e, 36f) configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 36f) are linear system actuators (36b, 36c, 36d, 36e, 36f) configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38a) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38a) (see FIG. 2) urges rotation of driven spool (98). In turn, shaft assembly (14), including proximal and distal shaft portions (60, 62)

rotates about longitudinal axis (61) as indicated by arrow (66) (see FIG. 3A), such as by robotically driven actuation of puck (38a) (see FIG. 2).

Linear system actuators (36b, 36c, 36d, 36e, 36f) of the present example include a gear-rack mechanism (102) having a rotatable drive gear (104), a translatable rack gear (106), and an idler gear (108) connected therebetween. Drive gears (104) are respectively connected to and rigidly project from pucks (38b, 38c, 38d, 38e, 38f) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38b, 38c, 38d, 38e, 38f) (see FIG. 2) thus respectively rotates drive gears (104) and idler gears (108) to translate rack gears (106) as desired.

In the present example, with respect to FIGS. 2-4B and FIG. 6, linear system actuator (36b) has puck (38b) operatively connected to clamp arm (44) to direct movement of clamp arm (44) between the open and closed positions according to arrow (52). Linear systems (36c, 36d) have respective pucks (38c, 38d) operatively connected to clamp arm (44) to direct movement of clamp arm (44) around blade (46) in both the clockwise and counterclockwise directions according to arrow (53). In addition, linear system actuators (36e, 36f) have respective pucks (38e, 38f) operatively connected to articulation bands (74) to direct movement of articulation section (64) according to arrows (88, 90) for deflecting end effector (16) relative to longitudinal axis (61). Of course, in other examples, instrument actuators (36a, 36b, 36c, 36d, 36c, 36f) may be alternatively configured with more or less actuators (36a, 36b, 36c, 36d, 36e, 36f) and/or more or less movement as desired. The invention is thus not intended to be unnecessarily limited to instrument actuators (36a, 36b, 36c, 36d, 36e, 36f) or particular movements of shaft assembly (14) and/or end effector (16) as described in the present example.

II. Exemplary End Effector with Axisymmetric Clamping

As mentioned above, clamp arm (44) is pivotally secured to a portion of shaft assembly (14) configured to longitudinally slide in order to pivot clamp arm (44), as indicated by arrow (52), between a closed position and an open position in order to engage tissue. As also mentioned above, clamp arm (44) is configured to rotate in the clockwise or counterclockwise directions completely around blade (46), as indicated by arrow (53) (i.e., clocking clamp arm (44)) into various clocked positions relative to blade (46).

In some instance, it may be desirable to have both features that pivot and clock clamp arm (44) driven by respectively separate linear system actuators (36b, 36c, 36d, 36e, 36f). However, it may be difficult or overly complicated to have the portion of shaft assembly (14) that pivots clamp arm (44) also rotate with clamp arm (44) into the various clocked positions. Therefore, it may be desirable to have the portion of shaft assembly (14) that pivots clamp arm (44) translate in order to pivot clamp arm (44) at any clocked position, without having to rotate with clamp arm (44) to the various clocked positions in order to maintain operable engagement with clamp arm (44). This may simplify the design of end effector (16) and distal shaft portion (62), as well as provide for a higher degree of precision for clamping of clamp arm (44).

Figure 7:
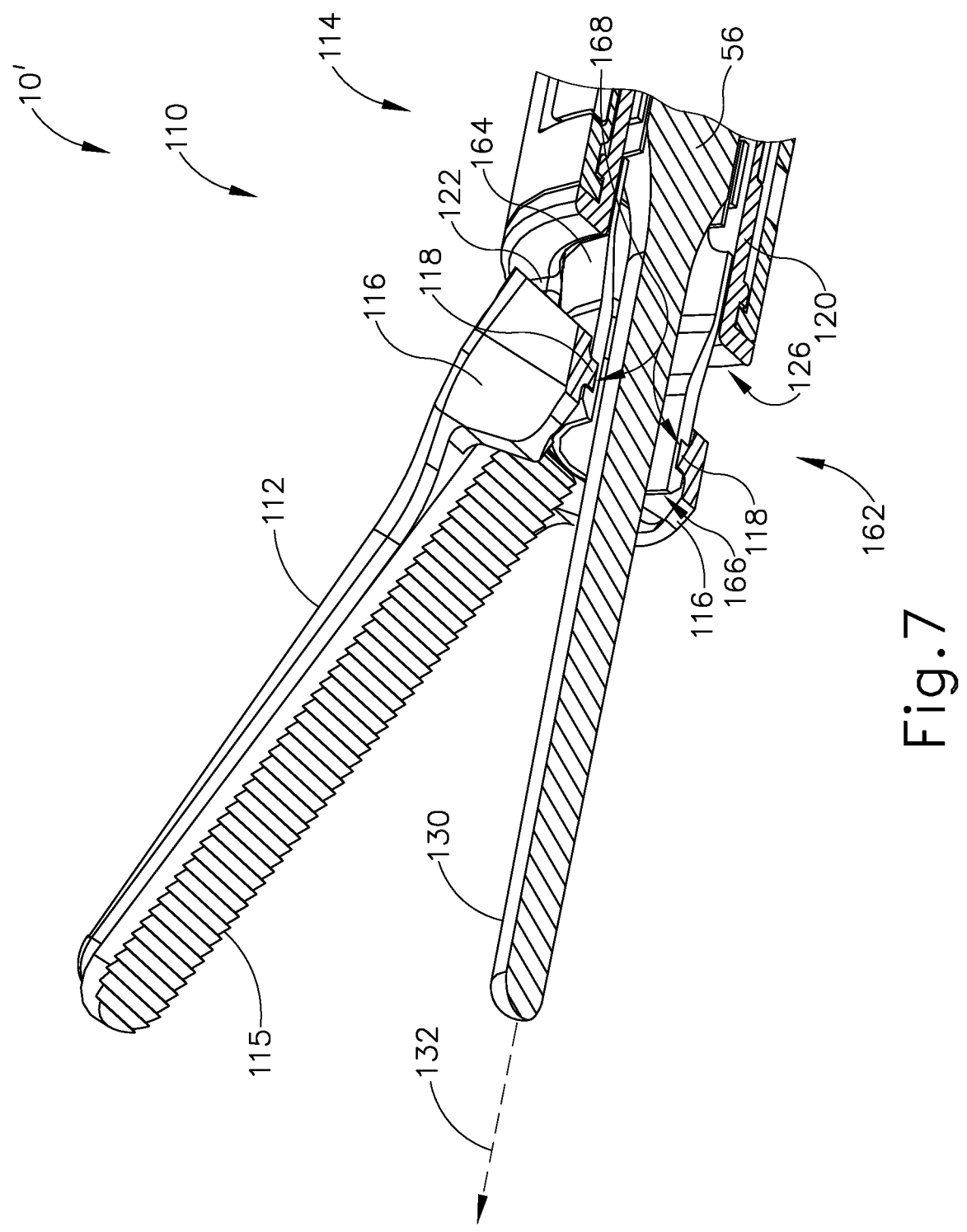
FIG. 7 depicts a sectional perspective view of an alternative end effector and alternative distal shaft portion that may be readily incorporated into the ultrasonic surgical instrument of FIG. 1.
Figure 8:
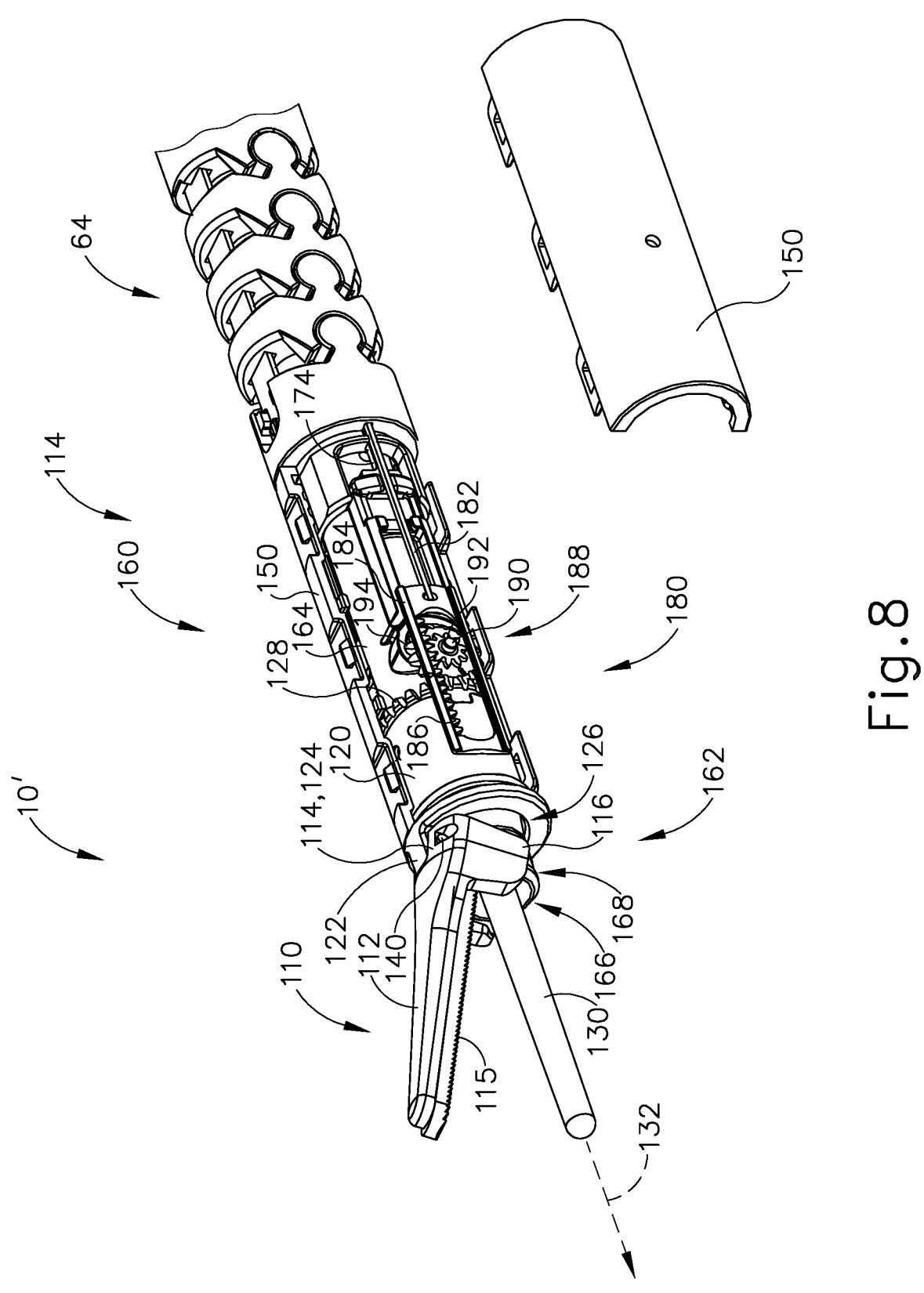
FIG. 8 depicts a partially exploded perspective view of the end effector and distal shaft portion of FIG. 7, showing a clamp arm closure assembly and a clamp arm clocking assembly.
Figure 9:
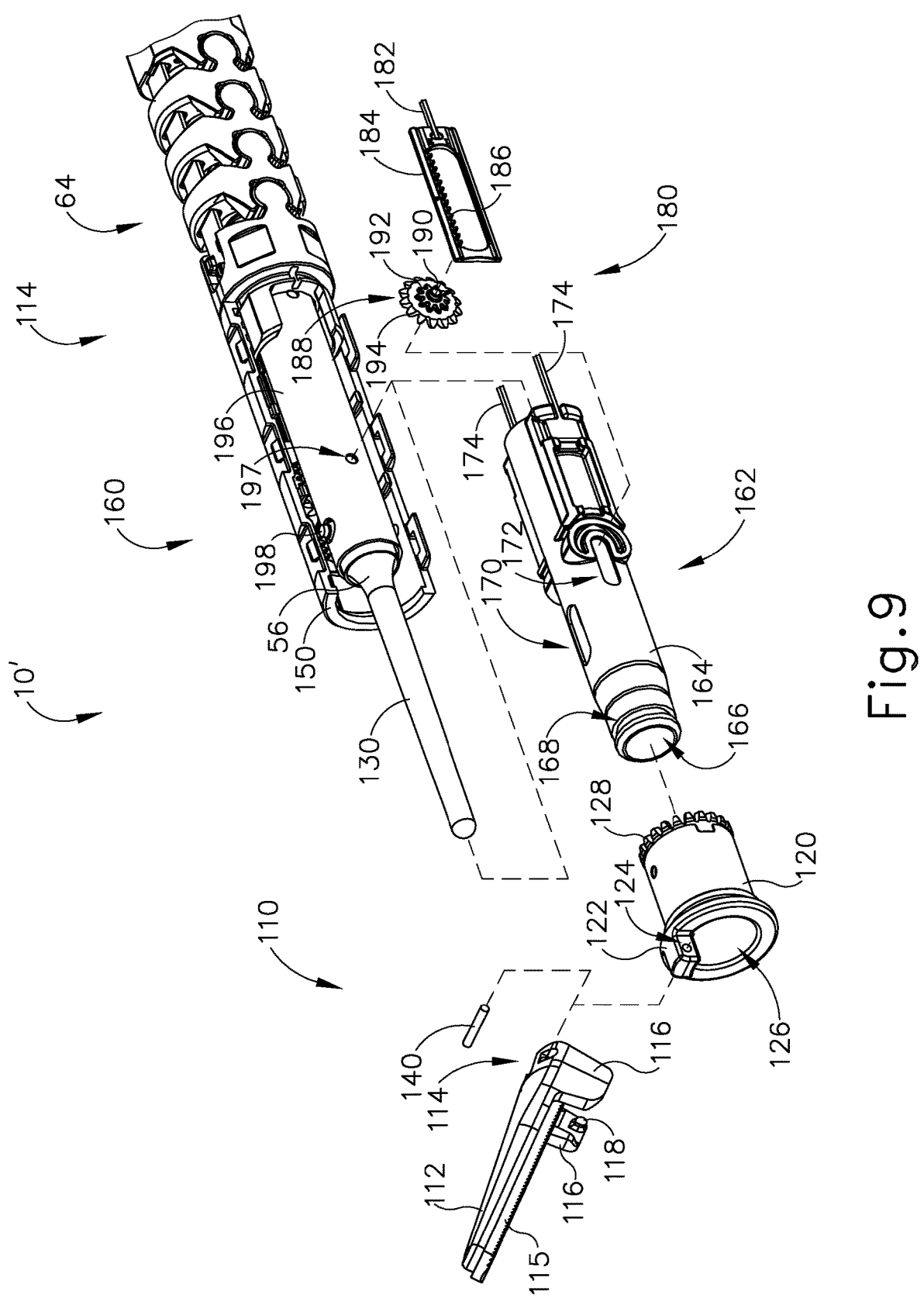
FIG. 9 depicts an exploded perspective view of the end effector and distal shaft portion of FIG. 7.
Figure 10:
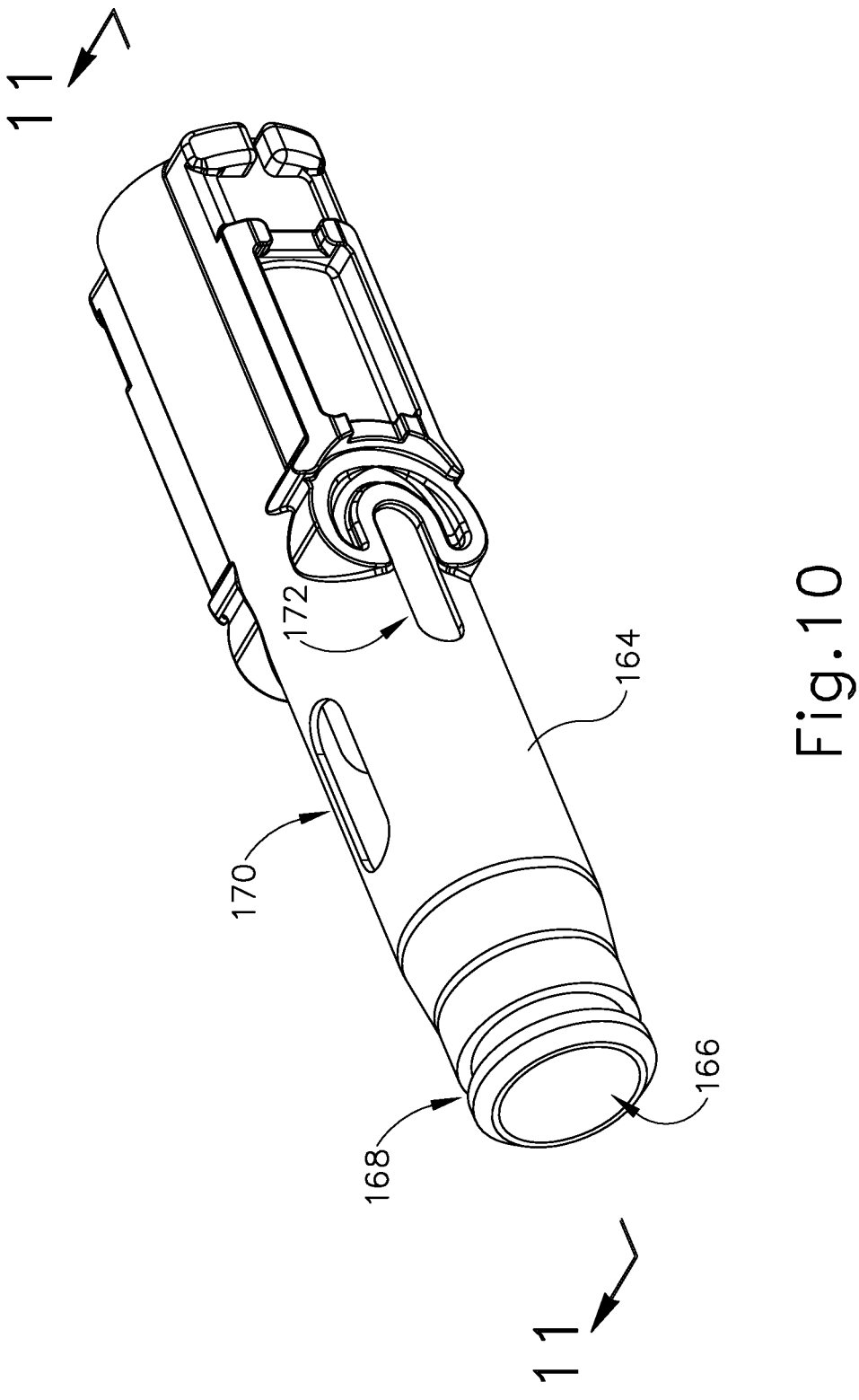
FIG. 10 depicts a perspective view of a translating body of the clamp arm closure assembly of FIG. 8.
Figure 11:
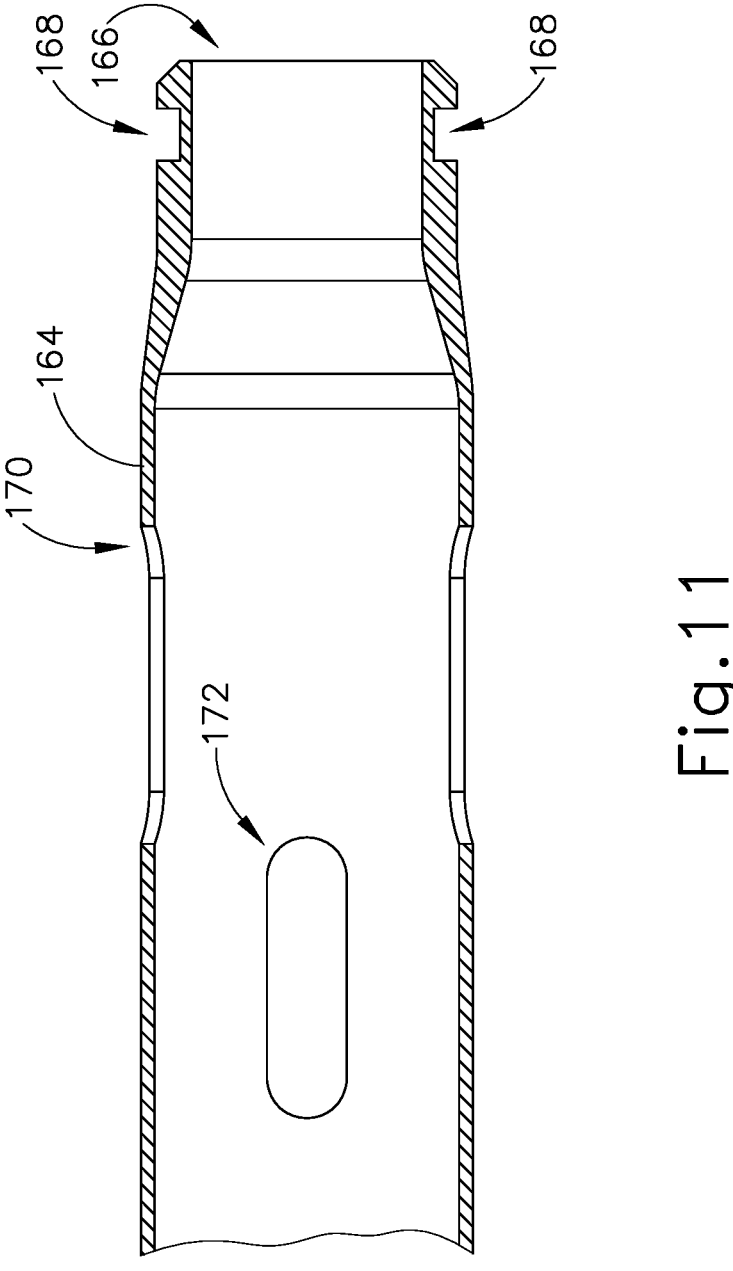
FIG. 11 depicts a cross-sectional view of the translating body of FIG. 10, taken along section line 11-11 of FIG. 10.
Figure 12:
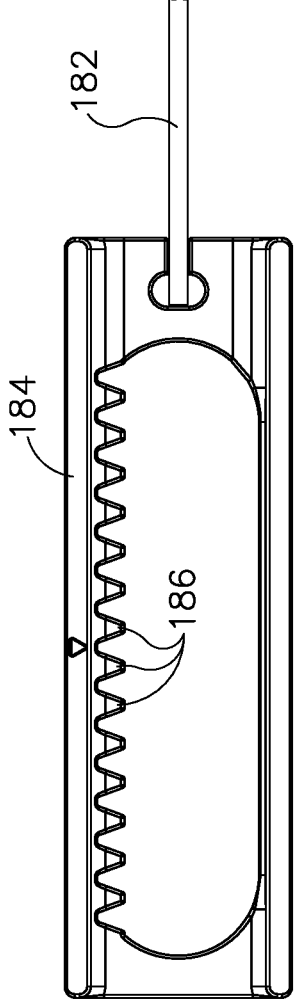
FIG. 12 depicts an elevational side view of a rack of the clamp arm clocking assembly of FIG. 8.
Figure 14:
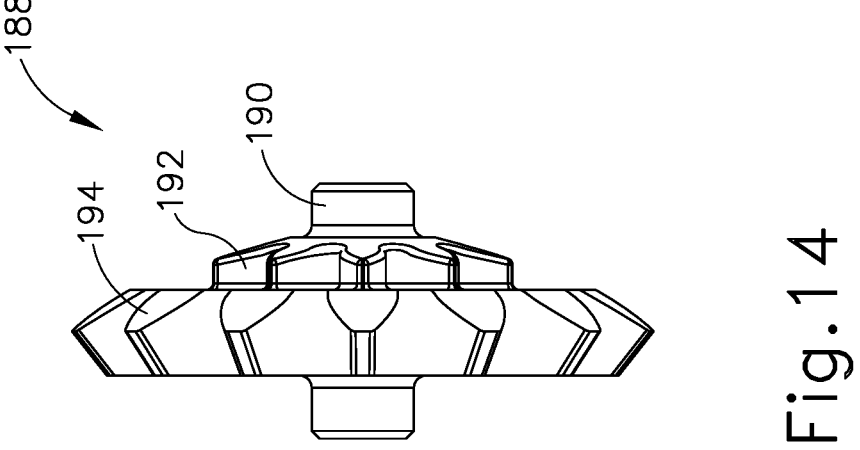
FIG. 14 depicts an elevational side view of the compound gear of FIG. 13.
Figure 13:
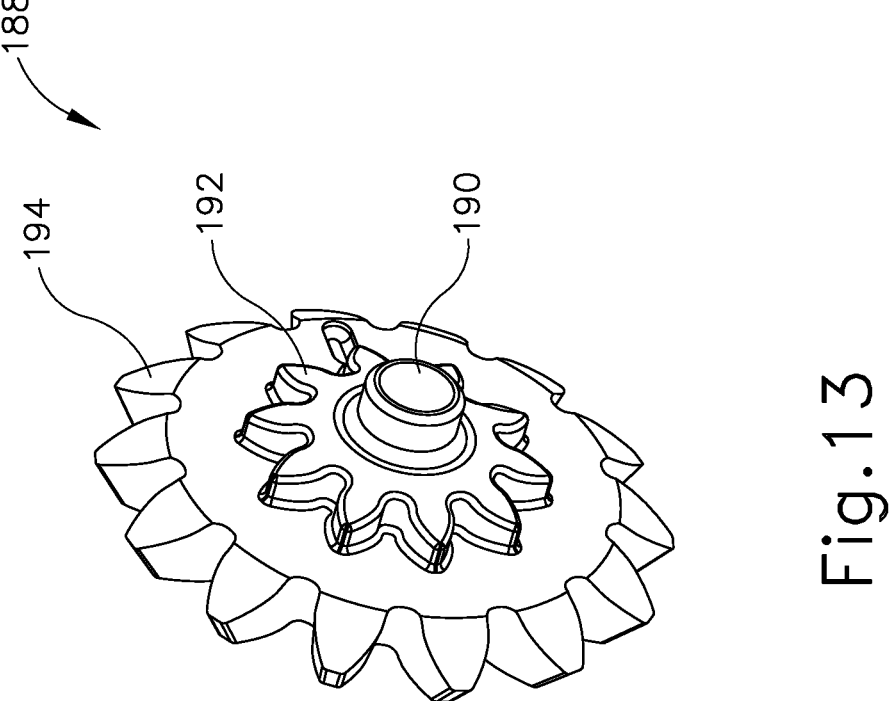
FIG. 13 depicts a perspective view of a compound gear of the clamp arm clocking assembly of FIG. 8.

FIGS. 7-9 show an alternative ultrasonic instrument (10') with an alternative end effector (110) and distal shaft portion (160) that may be readily incorporated into ultrasonic surgical instrument (10) (see FIG. 1) in replacement of end effector (16) and distal shaft portion (62) described above, respectively. As will be described in greater detail below, distal shaft portion (160) includes a clamp arm closure assembly (162) that is configured to translate in order to drive a clamp arm (112) of end effector (110) between an open position and closed position when clamp arm (112) is in various clocked positions. Additionally, as will be described in greater detail below, clamp arm closure assembly (162) remains operatively engaged with clamp arm (112) without having to follow clamp arm (112) into the various clocked positions.

A. Exemplary End Effector

End effector (110) includes clamp arm (112), clamp pad (115), a rotating body (120), and ultrasonic blade (130). Clamp arm (112), clamp pad (115), and ultrasonic blade (130) are substantially similar to clamp arm (44), clamp pad (48), and ultrasonic blade (46) described above, respectively, with differences elaborated below. Therefore, ultrasonic blade (130) is positioned at a distal end of an acoustic drivetrain. This acoustic drivetrain includes transducer assembly (54) (see FIG. 5) and acoustic waveguide (56), which includes flexible portion (58) (see FIG. 3A).

Clamp arm (112) is pivotally coupled to distally projecting tongue (122) of rotating body (120) via pin (140) and pin holes (114, 124). Therefore, clamp arm (112) may pivot about pin (140) relative to ultrasonic blade (130) between an open position (see FIGS. 17A-17B) and a closed position (see FIG. 17C). In the current example, pin (140) is housed within pin holes (114, 124) such that pin (140) does not move relative to pin holes (114, 124). However, pin (140) does not necessarily have to be fixed within pin hole (114, 124). Pin (140) may be a "floating pin" that may move within pin holes (114, 124) as clamp arm (112) pivots between the open position and the closed position. Additionally, or alternatively, clamp arm (112) may be pivotable relative to multiple axis/pins. Pin (140) may be coupled to rotating body (120) and clamp arm (112) through any suitable means as would be apparent to one skilled in the art in view of the teachings herein.

Clamp arm (112) also includes a pair of arms (116) that may be substantially similar to arms (51) described above, with differences elaborated below. Arms (116) include a respective inwardly presented protrusion (118) facing toward opposing arms (116). As best seen in FIG. 7, inwardly presented protrusions (118) are housed within an annular exterior channel (168) defined by a translating body (164) of clamp arm closure assembly (162). As will be described in greater detail below, actuation of translating body (164) along a path defined by axis (132) is configured to pivot clamp arm (112) between the open position and the closed position due to the interaction between inwardly presented protrusions (118) and annular exterior channel (168).

With respect to FIGS. 7-8, rotating body (120) includes distally presented tongue (122) defining pin hole (124) and a gear including an annular array of proximally facing teeth (128). Rotating body (120) is rotatably disposed within casings (150). As mentioned above, distally presented tongue (122) is configured to pivotably couple with clamp arm (112) via pin holes (114, 124) and pin (140). Therefore, as rotating body (120) rotates within casings (150) in accordance with the description herein, clamp arm (112) is rotated into various clocked positions. As will be described in greater detail below, proximally facing teeth (128) are configured to suitably mesh with a compound gear (188) of clamp arm clocking assembly (180) such that clocking assembly (180) may drive rotation of rotating body (120) about axis (132) relative to blade (130) in order to rotate clamp arm (112) about axis (132) relative to blade (130). As will also be described in greater detail below, inwardly presented protrusions (118) are configured to actuate within annular exterior channel (168) defined by translating body (164) as clamp arm (112) rotates about axis (132) relative to blade (130).

Figures 15, 16:
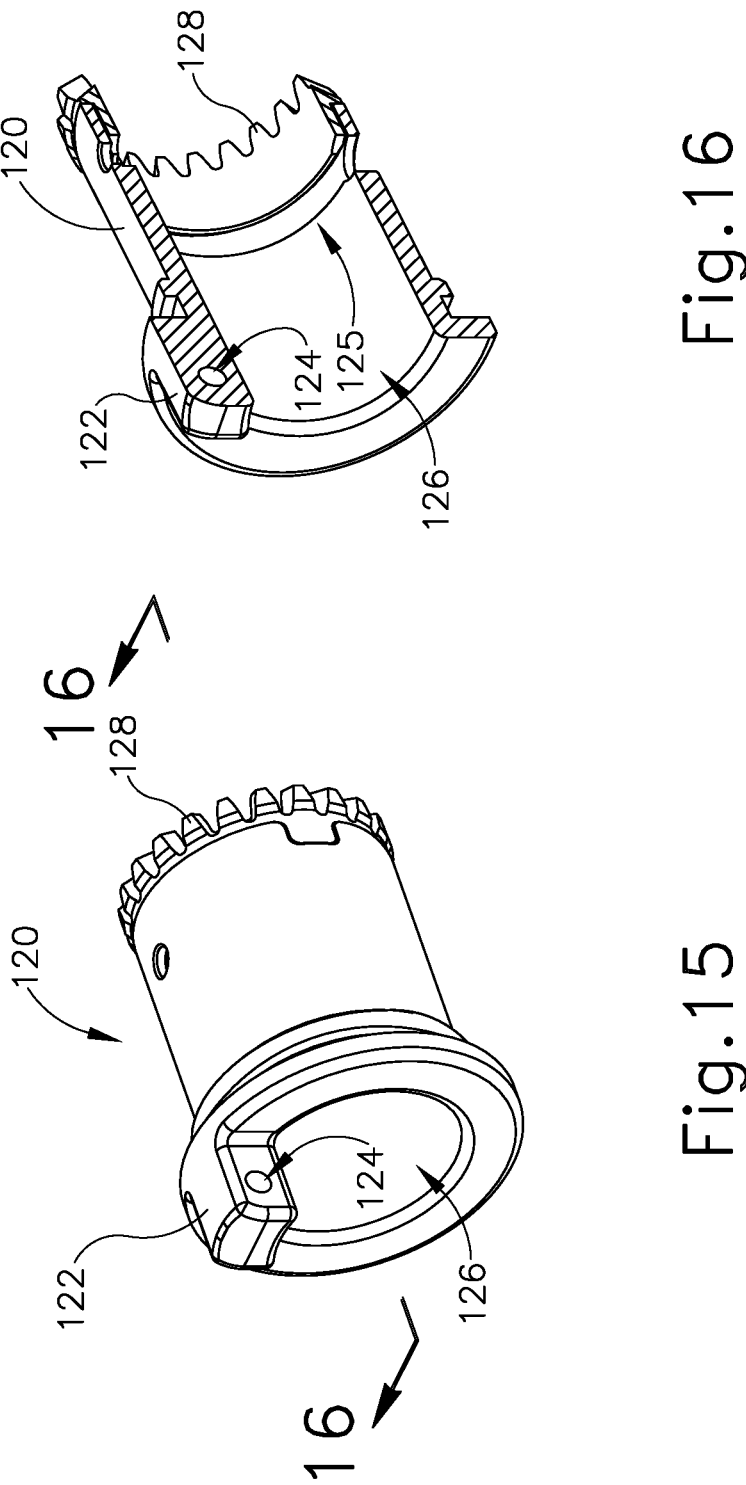
FIG. 15 depicts a perspective view of a rotating body of the end effector of FIG. 7.
FIG. 16 depicts a sectional perspective view of the rotating body of FIG. 15, taken along section line 16-16 of FIG. 15.

Rotating body (120) defines a hollow opening (126) extending from distally presented tongue (122) to proximally facing teeth (128). Hollow opening (126) is dimensioned to receive a portion of ultrasonic blade (130), a portion of waveguide (56), and translating body (164) of distal shaft portion (160). As best shown in FIGS. 9 and 16, an interior surface of rotating body (120) defining hollow opening (126) also defines an annular slot (125). Annular slot (125) is dimensioned to receive a waveguide pin (198) that extends through a distal portion of waveguide (56) and sleeve (196) of distal shaft portion (160). Therefore, rotating body (120) may be longitudinally fixed relative to waveguide (56) and blade (130), yet rotatable relative to waveguide (56) and blade (130) about axis (132). Pin (198) may extend through a nodal position of waveguide (56) during exemplary use. It should be understood the distal portion of waveguide (56) is distal relative to flexible portion (58) of waveguide (56).

B. Exemplary Distal Shaft Portion

As best seen in FIGS. 8-9, distal shaft portion (160) includes a pair of casings (150) that are configured to mate together in order to house various components of end effector (110) and distal shaft portion (160). A proximal end of each casing (150) is fixed to a distal end of articulation section (64). Therefore, as articulation section (64) articulates in accordance with the description above, distal shaft portion (160) and end effector (110) also deflects. Distal shaft portion (160) also includes sleeve (196), a clamp arm closure assembly (162), and a clamp arm clocking assembly (180). As mentioned above, sleeve (196) is coupled with waveguide (56) via waveguide pin (198). Therefore, sleeve (196) is configured to move with the associated portion of waveguide (56) as waveguide (56) rotates and articulates in accordance with the description herein.

As will be described in greater detail below, clamp arm clocking assembly (180) is configured to rotate clamp arm (112) and clamp pad (115) of end effector (110) about axis (132) defined by ultrasonic blade (130) in order to position clamp arm (112) and clamp pad (115) at various clocking positions relative to both blade (130) and clamp arm closure assembly (162) of distal shaft portion (160).

As will also be described in greater detail below, a clamp arm closure assembly (162) of distal shaft portion (160) is configured to translate in order to pivot clamp arm (112) and clamp pad (115) relative to ultrasonic blade (130) about an axis defined by pin (140) between an open position and a closed position. Additionally, clamp arm closure assembly (162) is operatively coupled with clamp arm (112) such that as clamp arm clocking assembly (180) rotates clamp arm (112) relative to blade (130) about axis (132), clamp arm closure assembly (162) remains operatively engaged with clamp arm (112) as well as in a substantially similar angular position relative to blade (130) about axis (132). In other words, clamp arm closure assembly (162) is configured to (i) remain in a substantially fixed angular position about axis (132) relative to blade (130) as clamp arm (112) rotates into various clocked positions, and (ii) pivot clamp arm (112) toward and away from blade (130), regardless of the clocked position of clamp arm (112). Allowing clamp arm closure assembly (162) to remain in the same rotational position about axis (132) relative to blade (130) while maintaining the functionality of pivoting clamp arm (112) about the axis defined by pin (140) may further simplify connections of clamp arm closure assembly (162) to various other parts of instrument (10) as well as provide for a higher degree of precision in clamping (i.e. pivoting clamp arm (112) from the open position to the closed position).

Clamp arm clocking assembly (180) includes a translating driver (182), a rack (184), and a compound gear (188). Translating driver (182) extends proximally through shaft assembly (14) and is operatively connected to at least one linear system actuator (36b, 36c, 36d, 36e, 36f) (see FIG. 6). Therefore, linear system actuator (36b, 36c, 36d, 36e, 36f) (see FIG. 6) coupled with the proximal end of translating driver (182) may actuate translating driver (182) proximally and distally relative to the rest of distal shaft portion (160). A distal end of translating driver (182) is fixed to rack (184) such that proximal and distal translation of translating driver (182) results in corresponding proximal and distal translation of rack (184). Rack (184) includes a linear array of teeth (186) that suitably mesh with teeth of a first gear (192) of compound gear (188). Therefore, translation of rack (184) results in rotation of compound gear (188).

Compound gear (188) includes a pin (190), first gear (192), and a second gear (194). Pin (190) extends along an axis through first gear (192) and second gear (194). Pin (190) is coupled with sleeve (196) via pin hole (197) such that suitable portions of compound gear (188) may rotate about the axis defined by pin (190) relative to sleeve (196) while inhibiting translation of compound gear (188) relative to sleeve (196). Pin (190) also extends through a longitudinal slot (172) defined by translating body (164). Longitudinal slot (172) is long enough to accommodate for translation of translating body (164), in accordance with the description herein, without unduly interfering with pin (190).

First gear (192) and second gear (194) are configured to rotate about an axis defined by pin (190). First gear (192) and second gear (194) are coupled with each other such that as first gear (192) rotates an angular displacement about the axis defined by pin (190), second gear (194) also rotates the same angular displacement about the axis defined by pin (190). Second gear (194) has a larger diameter compared to first gear (192), such that teeth of second gear (194) travel a further distance compared to teeth of first gear (192), even though both gears (192, 194) are rotated about pin (190) with the same angular displacement. Gears (192, 194) and pin (190) may be coupled with each other through any suitable means as would be apparent to one skilled in the art in view of the teachings herein.

As mentioned above, first gear (192) suitably meshes with teeth (186) of rack (184) such that proximal and distal translation of rack (184) rotates first gear (192) and second gear (194) about the axis defined by pin (190). As also mentioned above, rotating body (120) is rotatably disposed within casings (150) such that rotating body (120) may rotate about axis (132) defined by blade (130). Teeth of second gear (194) suitably mesh with proximally facing teeth (128) of rotating body (120) such that rotation of second gear (194) about the axis defined by pin (190) drives rotation of rotating body (120) about axis (132) defined by blade (130). Therefore, since clamp arm (112) is coupled to rotating body (120), translation of rack (184) in the proximal direction and the distal direction is configured to rotate rotating body (120) and clamp arm (112) about axis (132) defined by blade (130) in a first rotational direction and a second, opposite, rotational direction, respectively. In other words, translation of translating driver (182) is configured to change the clocked position of clamp arm (112) relative to blade (130).

Rack (184) and compound gear (188) are configured to rotate with sleeve (196) in accordance with the description herein. Therefore, when waveguide (56) rotates in the direction indicated by arrow (66) (see FIG. 3A), rack (184) and compound gear (188) also rotate in the direction indicated by arrow (66) (see FIG. 3A). Engagement between second gear (194) and proximally facing teeth (128) may drive rotating body (120) and clamp arm (112) to also rotate with waveguide (56) in the direction indicated by arrow (66) (see FIG. 3A). Therefore, when waveguide (56) is rotated in the direction indicated by arrow (66) (see FIG. 3A), clamp arm (112) may remain in the same clocked position relative to blade (130).

While in the current example, rack (184), compound gear (188), and proximally facing teeth (128) are used to convert translation of translating driver (182) into rotation of clamp arm (112) about blade (130), any other suitable means may be used to rotate clamp arm (112) about blade (130) as would be apparent to one skilled in the art in view of the teachings herein. Therefore, when a shaft assembly (14) rotates in the direction indicated by arrow (66) (see FIG. 3A), distal shaft portion (160) and end effector (110) may also rotate in the direction indicated by arrow (66) (see FIG. 3A).

Clamp arm closure assembly (162) includes translating body (164) and translating drivers (174). Similar to translating driver (182) described above, translating drivers (174) extend proximally through shaft assembly (14) and are operatively connected to at least one linear system actuator (36b, 36c, 36d, 36e, 36f) other than linear system actuator (36b, 36c, 36d, 36e, 36f) coupled to translating drivers (182). Therefore, linear system actuator (36b, 36c, 36d, 36e, 36f) coupled with the proximal end of translating drivers (174) may actuate translating drivers (174) proximally and distally relative to the rest of distal shaft portion (160) independently of translating driver (182). Distal ends of translating drivers (174) are fixed to translating body (164) such that proximal and distal translation of translating drivers (174) results in corresponding proximal and distal translation of translating body (164).

Translating body (164) defines a hollow opening (166), annular exterior channel (168), a first longitudinal slot (170), and second longitudinal slot (172). Hollow opening (166) extends from a proximal end to a distal end of translating body (164). Hollow opening (166) is dimensioned to slidably receive sleeve (196) such that translating body (164) may actuate relative to sleeve (196) and blade (130).

First longitudinal slot (170) is dimensioned to house waveguide pin (198) such that translating body (164) may translate relative to sleeve (196) and blade (130), but such that translating body (164) is rotationally fixed relative to sleeve (196) and blade (130). In other words, as waveguide (56) and blade (130) are rotated in the direction indicated by arrow (66) (see FIG. 3A) in accordance with the description herein, waveguide pin (198) drives corresponding rotation of sleeve (196) and translating body (164). Annular exterior channel (168) operatively houses inwardly presented protrusions (118) such that translation of body (164) drives clamp arm (112) to pivot about pin (140). Therefore, translating body (164) may be driven proximally and distally via translating drivers (174) in order to pivot clamp arm (112) about pin (140) toward and away from blade (130).

Additionally, annular exterior channel (168) is configured to operatively house inwardly presented protrusions (118) as clamp arm (112) is clocked in various positions about axis (132) in accordance with the description herein. Therefore, annular exterior channel (168) acts as a track to retain inwardly presented protrusions (118). Because annular exterior channel (168) can operatively house inwardly presented protrusion (118) as clamp arm (112) is clocked in various positions relative to blade (130) about axis (132), translating body (164) may retain the ability to pivot clamp arm (112) in a plurality of clocked positions without having to rotate with clamp arm (112) about axis (132). Allowing translating body (164) to retain the ability to pivot clamp arm (112) in a plurality of clocked positions without having to rotate with clamp arm (112) about axis (132) may provide for a higher degree of precision for pivoting clamp arm (112) about pin (140).

In the current example, annular exterior channel (168) extends all the way around a circumferential portion of translating body (164) such that annular exterior channel (168) is continuous, however this is merely optional. Annular exterior channel (168) may extend circumferentially around only a portion of translating body (164) in order to accommodate the various intended clocking position of clamp arm (112). For instance, in some embodiments, annular exterior channel (168) may extend circumferentially around a portion of translating body (164) such that terminating ends of annular exterior channel (168) are 180 degrees apart.

Figure 17A:
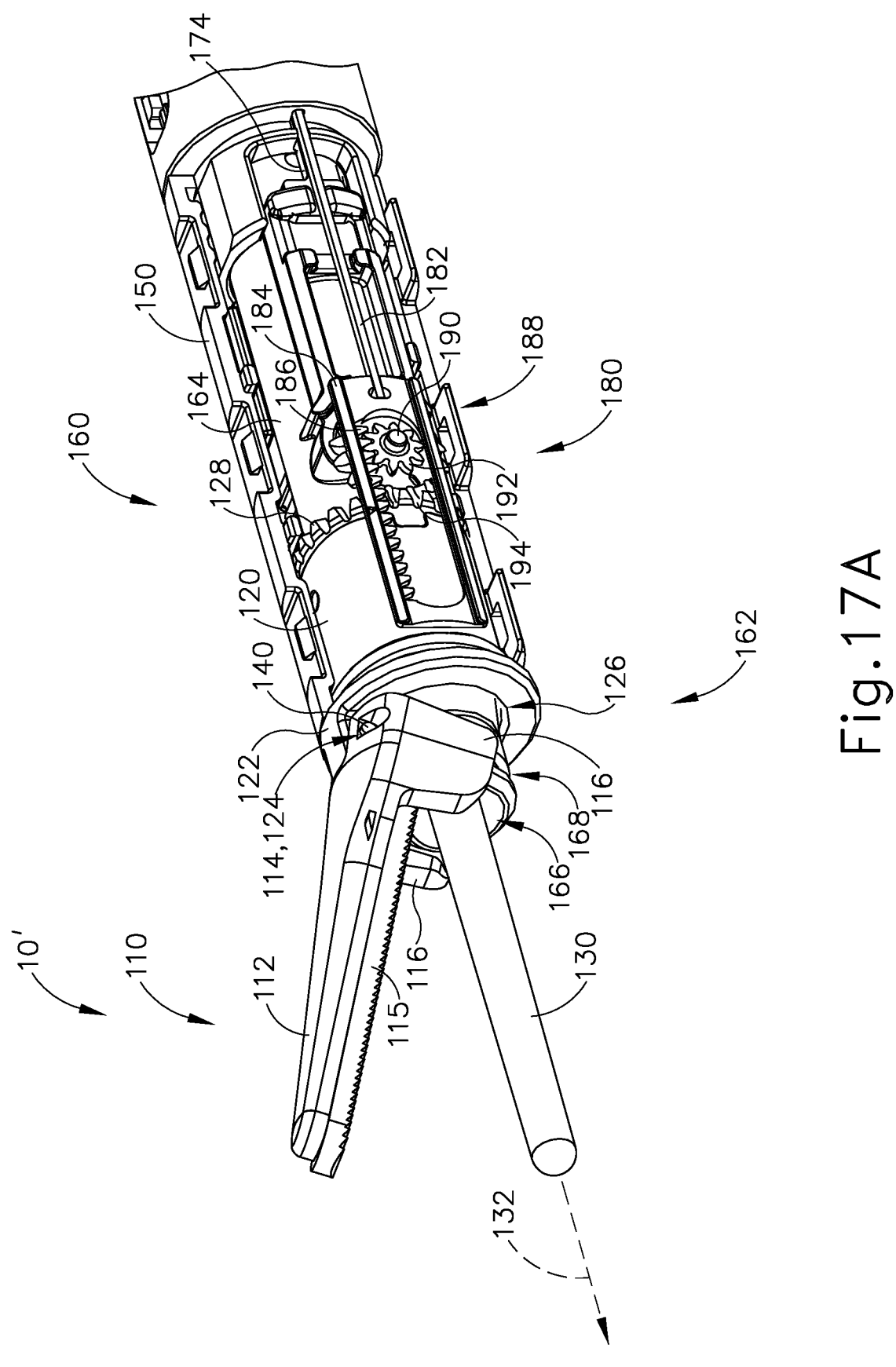
FIG. 17A depicts a perspective view of the end effector and distal shaft portion of FIG. 7, with certain portions omitted for clarity; where a clamp arm of the end effector of FIG. 7 is in an open position in a first clocked position.
Figure 17B:
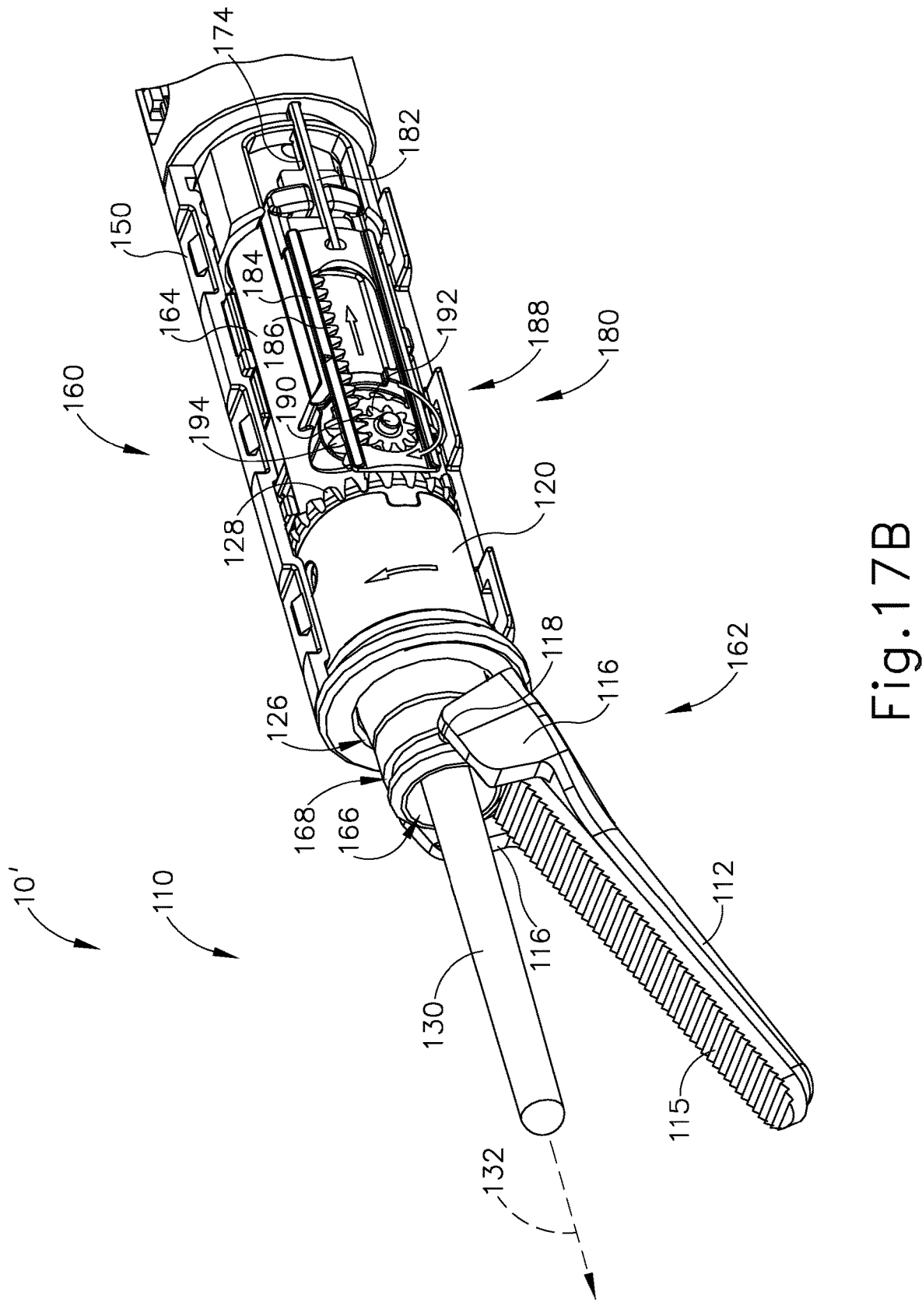
FIG. 17B depicts a perspective view of the end effector and distal shaft portion of FIG. 7, with certain portions omitted for clarity where the clamp arm of FIG. 17A is in the open position in a second clocked position.
Figure 17C:
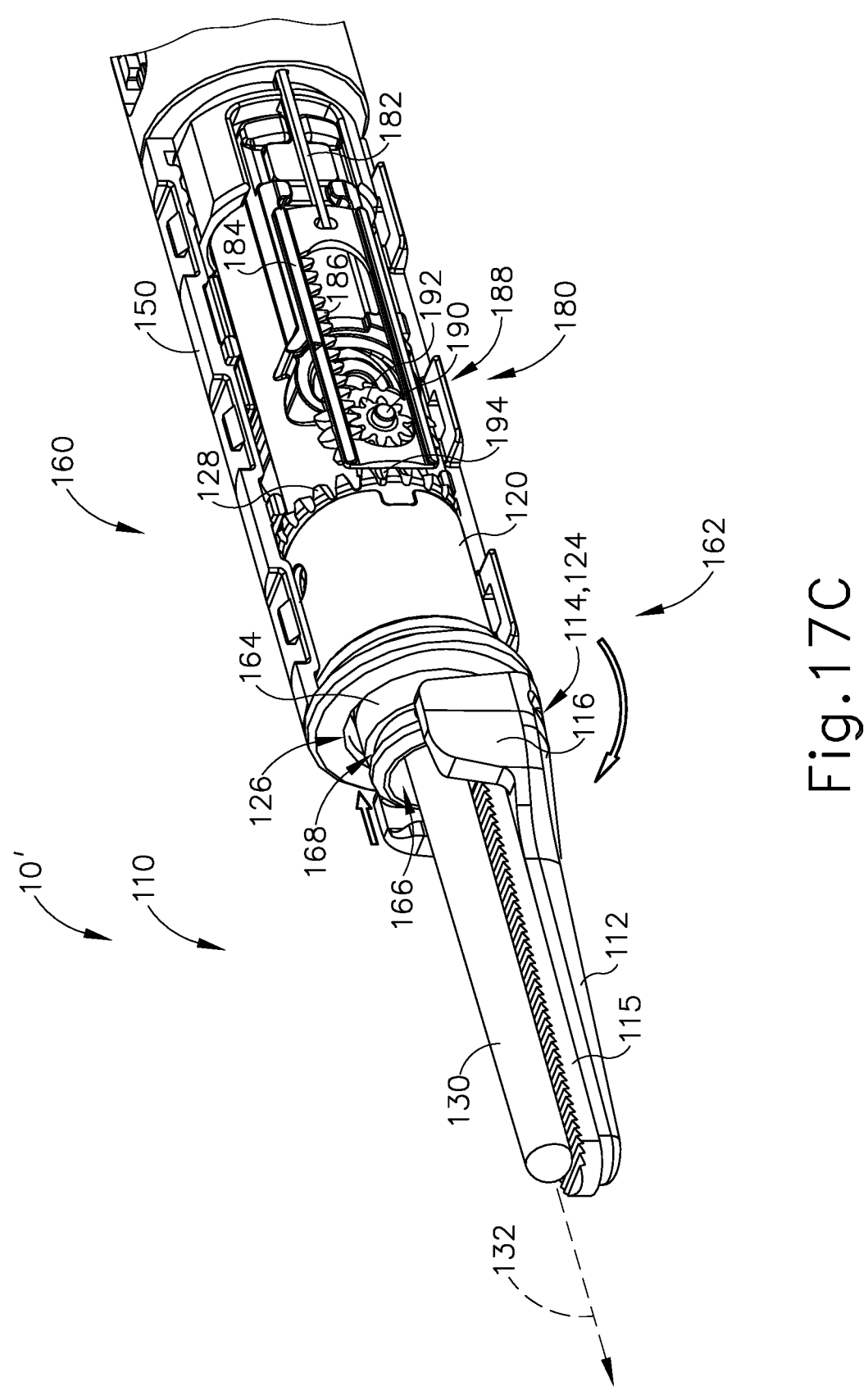
FIG. 17C depicts a perspective view of the end effector and distal shaft portion of FIG. 7, with certain portions omitted for clarity where the clamp arm of FIG. 17A is in a closed position in the second clocked position.

FIGS. 17A-17C show an exemplary use of clamp arm clocking assembly (180) and clamp arm closure assembly (162) being used in order to rotate clamp arm (112) about blade (130) (See FIGS. 17A-17B), and then pivot clamp arm (112) about pin (140) in order to drive clamp arm (112) from the open position to the closed position (See FIGS. 17B-17C). FIG. 17A shows clamp arm (112) in the open position and a first clocked position relative to blade (130). If the operator desires to change the clocked position of clamp arm (112), the operator may instruct instrument (10') to drive translating driver (182) proximally, which in turn rotates rotating body (120) and clamp arm (112) about blade (130) into a second clocked position.

It should be understood that as clamp arm (112) is rotated about blade (130) into the second clocked position, inwardly presented protrusions (118) are still operatively housed within annular exterior channel (168) of translating body (164). It should also be understood that translating body (164) remains in the same angular position about axis (132) of blade (130) as clamp arm (112) is rotated into the second clocked position. If the operator desires to rotate clamp arm (112) back toward the first clocked position, the operator may instruct instrument (10') to drive translating driver (182) distally until clamp arm (112) is driven into the desired clocked position.

Next, with clamp arm (112) rotated about blade (130) into the desired clocked position, the operator may instruct instrument (10') to drive translating drivers (174) and translating body (164) proximally, which in turn pivots clamp arm (112) to the closed position. It should be understood that since inwardly presented protrusions (118) are operatively housed within annular exterior channel (168) while clamp arm (112) is in any clocked position, proximal translation of translating body (164) drives protrusions (118) proximally, which in turn pivots clamp arm (112) about pin (140) into the closed position. If the operator desires to pivot clamp arm (112) back toward the open position, the operator may instruct instrument (10') to drive translating drivers (174) distally until clamp arm (112) is pivoted about pin (140) into the desired position.

It should be understood that the operator may rotate clamp arm (112) to the second locked position while clamp arm (112) is in the closed position as well. In the current example, clamp arm (112) is rotated about blade (130) 180 degrees from the first clocked position. Clamp arm (112) may be rotated about blade (130) to any other suitably clocked position as would be apparent to one skilled in the art in view of the teachings herein. In the current example, rack (184) extends along a length to rotate clamp arm (112) a maximum of 180 degrees about blade (130). It should be understood that rack (184) may have any suitable length to rotate clamp arm (112) about blade (130) at any suitable angular displacement as would be apparent to one skilled in the art in view of the teachings herein. For instance, rack (184) may have a suitable length to rotate clamp arm (112) 360 degrees about blade (130).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector, comprising: (i) an ultrasonic blade, (ii) a rotating body configured to rotate relative to the ultrasonic blade, and (iii) a clamp arm movably coupled to the rotating body, wherein the clamp arm is configured to move relative to the rotating body and the ultrasonic blade between an open position and a closed position; and (b) a shaft assembly extending along an axis, the shaft assembly comprising: (i) a clamp arm clocking assembly configured to drive rotation of the rotating body and the clamp arm about the axis relative to the ultrasonic blade between a first clocked position and a second clocked position, and (ii) a clamp arm pivot assembly comprising an actuator body located in a first rotational position relative to the ultrasonic blade about the axis, wherein the actuator body is configured to actuate between a distal position and a proximal position in order to drive the clamp arm between the open position and the closed position, wherein the actuator body defines a track housing a portion of the clamp arm, wherein the track is configured to house the portion of the clamp arm when the clamp arm is in the first clocked position and the second clocked position while the actuator body is located in the first rotational position.

Example 2

The surgical instrument of Example 1, wherein the portion of the clamp arm housed within the track comprises a first protrusion and a second protrusion.

Example 3

The surgical instrument of Example 2, wherein the clamp arm comprises a first arm and a second arm, wherein the first protrusion is attached to the first arm, wherein the second protrusion is attached to the second arm.

Example 4

The surgical instrument of Example 3, wherein the first protrusion and the second protrusion face toward each other.

Example 5

The surgical instrument of any one or more of Examples 1 through 4, wherein the track comprises an annular channel.

Example 6

The surgical instrument of Example 5, wherein the annular channel is continuous.

Example 7

The surgical instrument of Example 5, wherein the annular channel is located on an exterior surface of the actuator body.

Example 8

The surgical instrument of any one or more of Examples 1 through 7, wherein the actuator body comprises a tubular body.

Example 9

The surgical instrument of any one or more of Examples 1 through 8, further comprising a waveguide in acoustic communication with the ultrasonic blade, wherein a pin extends through the waveguide.

Example 10

The surgical instrument of Example 9, wherein the actuating body defines a first longitudinal slot, wherein the pin extends into the longitudinal slot, wherein the pin is configured to fix the actuating body in the first rotational position.

Example 11

The surgical instrument of Example 10, wherein the rotating body defines an annular slot, wherein the pin is housed within the annular slot.

Example 12

The surgical instrument of any one or more of Examples 1 through 11, wherein the rotating body comprises a distally presented tongue, wherein the clamp arm is pivotably coupled with the distally presented tongue.

Example 13

The surgical instrument of Example 12, wherein the clamp arm is pivotably coupled with the distally presented tongue via a pivot pin.

Example 14

The surgical instrument of any one or more of Examples 1 through 13, wherein the clamp arm clocking assembly comprises a rack and a compound gear, wherein the rack is configured to translate in order to rotate the compound gear.

Example 15

The surgical instrument of Example 14, wherein the compound gear is operatively coupled with the rotating body, wherein the compound gear is configured to rotate the rotating body.

Example 16

A surgical instrument, comprising: (a) an end effector, comprising: (i) an ultrasonic blade, (ii) a rotating body disposed around a portion of the ultrasonic blade, wherein the rotating body is configured to rotate around the portion of the ultrasonic blade, and (iii) a clamp arm pivotably coupled to the rotating body, wherein the clamp arm is configured to pivot relative to the rotating body and the ultrasonic blade between an open position and a closed position, wherein the clamp arm is configured to rotate around the ultrasonic blade between a first clocked position and a second clocked position; (b) an actuator body configured to translate relative to the ultrasonic blade while located in a first rotational position relative to the ultrasonic blade, wherein the actuator body defines a track housing a portion of the clamp arm, wherein the actuator body is configured to actuate the portion of the clamp arm in order to drive the clamp arm between the open position and the closed position, wherein the track is configured to house the portion of the clamp arm when the clamp arm is in the first clocked position and the second clocked position while the actuator body is located in the first rotational position.

Example 17

The surgical instrument of Example 16, wherein the actuator body is disposed around a portion of the ultrasonic blade.

Example 18

The surgical instrument of any one or more of Examples 16 through 17, wherein the track extends along an exterior portion of the actuator body.

Example 19

The surgical instrument of any one or more of Examples 16 through 18, further comprising a translating driver attached to the actuator body, wherein the translating driver is configured to actuate the actuator body relative to the ultrasonic blade.

Example 20

A surgical instrument, comprising: (a) an end effector, comprising: (i) an ultrasonic blade extending along an axis, (ii) a clamp arm configured to pivot relative to the ultrasonic blade between an open position and a closed position, wherein the clamp arm is configured to rotate around the axis relative to the ultrasonic blade between a first clocked position and a second clocked position; (b) an actuator body configured to translate relative to the ultrasonic blade while located in a first rotational position relative to the ultrasonic blade, wherein the actuator body defines a track housing a portion of the clamp arm, wherein the actuator body is configured to actuate the portion of the clamp arm in order to drive the clamp arm between the open position and the closed position, wherein the track is configured to house the portion of the clamp arm when the clamp arm is in the first clocked position and the second clocked position while the actuator body is located in the first rotational position.

IV. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, published as U.S. Pub. No. 2021/0059709 on Mar. 4, 2021, issued as U.S. Pat. No. 11,690,642 on Jul. 4, 2023; U.S. patent application Ser. No. 16/556,667 entitled "Ultrasonic Transducer Alignment of an Articulating Ultrasonic Surgical Instrument," filed on Aug. 30, 2019, published as U.S. Pub. No. 2021/0059710 on Mar. 4, 2021, issued as U.S. Pat. No. 11,612,409 on Mar. 28, 2023; U.S. patent application Ser. No. 16/556,635, entitled "Ultrasonic Blade and Clamp Arm Alignment Features," filed on Aug. 30, 2019, published as U.S. Pub. No. 2021/0059708 on Mar. 4, 2021, issued as U.S. Pat. No. 11,457,945 on Oct. 4, 2022; and/or U.S. patent application Ser. No. 16/556,727 entitled "Rotatable Linear Actuation Mechanism," filed on Aug. 30, 2019, published as U.S. Pub. No. 2021/0059711 on Mar. 4, 2021, issued as U.S. Pat. No. 11,712,261 on Aug. 1, 2023. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873, 873; 5,980,510; 6,325,811; 6,773,444; 6,783,524; 9,095, 367; U.S. Pub. No. 2006/0079874, now abandoned; U.S. Pub. No. 2007/0191713, now abandoned; U.S. Pub. No. 2007/0282333, now abandoned; U.S. Pub. No. 2008/ 0200940, now abandoned; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265, now abandoned; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACER Ultrasonic Shears, the HARMONIC WAVER Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACER Ultrasonic Shears, the HARMONIC WAVER Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACER Ultrasonic Shears, the HARMONIC WAVER Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
(a) an end effector, comprising:
   (i) an ultrasonic blade,
   (ii) a rotating body configured to rotate relative to the ultrasonic blade, and
   (iii) a clamp arm movably coupled to the rotating body, wherein the clamp arm is configured to move relative to the rotating body and the ultrasonic blade between an open position and a closed position; and
(b) a shaft assembly extending along a shaft axis, the shaft assembly comprising:
   (i) an articulation joint configured to articulate the rotating body along a plane, and
   (ii) a clamp arm clocking assembly including a rotating gear and configured to drive rotation of the rotating body and the clamp arm about the shaft axis relative to the ultrasonic blade between a first clocked position and a second clocked position, wherein the rotating gear is rotatable about a rotation axis perpendicular to the plane.

2. The surgical instrument of claim 1, wherein the rotating gear includes a first set of teeth configured to be driven by a rack.

3. The surgical instrument of claim 2, wherein the rack is configured to translate parallel to the shaft axis.

4. The surgical instrument of claim 2, wherein the rotating gear includes a second set of teeth configured to drive rotation of the rotating body and the clamp arm about the shaft axis relative to the ultrasonic blade.

5. The surgical instrument of claim 4, wherein the rotating body includes a ring gear annularly positioned about the shaft axis and configured to mesh with the second set of teeth of the rotating gear.

6. The surgical instrument of claim 1, wherein the clamp arm is pivotable about the rotating body.

7. The surgical instrument of claim 1, the shaft assembly further comprising a clamp arm pivot assembly comprising an actuator body, wherein the actuator body is configured to actuate between a distal position and a proximal position in order to drive the clamp arm between the open position and the closed position, wherein the actuator body defines a track housing a portion of the clamp arm, wherein the track is configured to house the portion of the clamp arm when the clamp arm is in the first clocked position and the second clocked position.

8. The surgical instrument of claim 7, wherein the clamp arm pivot assembly defines a longitudinal slot, wherein the rotating gear includes a pin, wherein the pin is translatable relative to the clamp arm pivot assembly and within the longitudinal slot.

9. The surgical instrument of claim 7, wherein the clamp arm pivot assembly is configured to actuate between the distal position and the proximal position while being positioned within the rotating body.

10. The surgical instrument of claim 7, wherein the clamp arm pivot assembly defines a longitudinal slot, wherein the ultrasonic blade includes a waveguide pin translatable within the longitudinal slot to thereby rotational fix the ultrasonic blade to the clamp arm pivot assembly.

11. A surgical instrument, comprising:
(a) an end effector, comprising:
(i) an ultrasonic blade,
(ii) a rotating body configured to rotate relative to the ultrasonic blade, and
(iii) a clamp arm movably coupled to the rotating body, wherein the clamp arm is configured to move relative to the rotating body and the ultrasonic blade between an open position and a closed position; and
(b) a shaft assembly extending along a shaft axis, the shaft assembly comprising:
(i) a clamp arm pivot assembly comprising an actuator body, wherein the actuator body is configured to actuate between a distal position and a proximal position in order to drive the clamp arm between the open position and the closed position, and
(ii) a clamp arm clocking assembly including a rotating gear and configured to drive rotation of the rotating body and the clamp arm about the shaft axis relative to the ultrasonic blade between a first clocked position and a second clocked position, wherein the rotating gear is translatable relative to the clamp arm pivot assembly,
wherein the rotating gear includes a first set of teeth configured to drive rotation of the rotating body and the clamp arm about the shaft axis relative to the ultrasonic blade.

12. The surgical instrument of claim 11, wherein the rotating gear includes a second set of teeth configured to be driven by a rack.

13. The surgical instrument of claim 12, wherein the rack is configured to translate relative to the clamp arm pivot assembly.

14. The surgical instrument of claim 11, wherein the rotating body includes a ring gear annularly positioned about the shaft axis and configured to mesh with the first set of teeth of the rotating gear.

15. The surgical instrument of claim 11, wherein the clamp arm is pivotable about the rotating body.

16. The surgical instrument of claim 11, wherein the clamp arm pivot assembly defines a longitudinal slot, wherein the rotating gear includes a pin, wherein the pin is translatable relative to the clamp arm pivot assembly and within the longitudinal slot.

17. A surgical instrument, comprising:
(a) an end effector, comprising:
(i) an ultrasonic blade,
(ii) a rotating body configured to rotate relative to the ultrasonic blade, and
(iii) a clamp arm movably coupled to the rotating body, wherein the clamp arm is configured to move relative to the rotating body and the ultrasonic blade between an open position and a closed position; and
(b) a shaft assembly extending along a shaft axis, the shaft assembly comprising:
(i) an articulation joint configured to articulate the rotating body along a plane, and
(ii) a clamp arm pivot assembly comprising an actuator body, wherein the actuator body is configured to actuate between a distal position and a proximal position in order to drive the clamp arm between the open position and the closed position, wherein the actuator body is rotationally fixed to the ultrasonic blade.

18. The surgical instrument of claim 17, the shaft assembly further comprising a clamp arm clocking assembly configured to drive rotation of the rotating body and the clamp arm about the shaft axis relative to the ultrasonic blade between a first clocked position and a second clocked position, wherein a rotating gear of the clamp arm clocking assembly is rotatable about a rotation axis perpendicular to the plane, wherein the clamp arm pivot assembly defines a longitudinal slot, wherein the rotating gear includes a pin, wherein the pin is translatable relative to the clamp arm pivot assembly and within the longitudinal slot.

19. The surgical instrument of claim 17, wherein the clamp arm is pivotable about the rotating body.

\* \* \* \* \*